United States Patent [19]

Bigorra Llosas et al.

[11] Patent Number: 6,028,229

[45] Date of Patent: Feb. 22, 2000

[54] PROCESS FOR PRODUCING END-GROUP-LOCKED NON-IONIC TENSIDES

[75] Inventors: Joaquim Bigorra Llosas, Sabadell; Nuria Bonastre, Barbera del Valles; Rafael Pi Subirana, Granollers; Antonio Trius Oliva, Valldoreix, all of Spain

[73] Assignee: Henkel Kommanditgesellschaft auf Aktien, Duesseldorf, Germany

[21] Appl. No.: 08/860,891

[22] PCT Filed: Dec. 27, 1995

[86] PCT No.: PCT/EP95/05139

§ 371 Date: Aug. 11, 1997

§ 102(e) Date: Aug. 11, 1997

[87] PCT Pub. No.: WO96/21636

PCT Pub. Date: Jul. 18, 1996

[30] Foreign Application Priority Data

Jan. 13, 1995 [DE] Germany .......................... 195 00 842

[51] Int. Cl.⁷ .................................................... C07C 43/11
[52] U.S. Cl. .......................... 568/618; 568/616; 568/617; 252/351; 252/329
[58] Field of Search ..................... 568/618, 617, 568/616; 252/329, 351

[56] References Cited

U.S. PATENT DOCUMENTS

| | | | |
|---|---|---|---|
| 4,548,729 | 10/1985 | Schmid et al. | 252/174.21 |
| 4,587,365 | 5/1986 | Archor | 568/619 |
| 4,922,029 | 5/1990 | Birnbach et al. | 568/616 |
| 4,942,049 | 7/1990 | Schmid et al. | 426/329 |
| 4,973,423 | 11/1990 | Geke et al. | 252/174.21 |
| 5,484,553 | 1/1996 | Guth et al. | 252/351 |

FOREIGN PATENT DOCUMENTS

| | | |
|---|---|---|
| 0 124 815 | 11/1984 | European Pat. Off. . |
| 0 302 487 | 2/1989 | European Pat. Off. . |
| 0 303 928 | 2/1989 | European Pat. Off. . |
| 0 324 340 | 7/1989 | European Pat. Off. . |
| 0 420 802 | 4/1991 | European Pat. Off. . |
| 0 427 088 | 5/1991 | European Pat. Off. . |
| 427088 | 5/1991 | European Pat. Off. ........ C08G 65/32 |
| 26 56 727 | 6/1978 | Germany . |
| 39 28 600 | 3/1991 | Germany . |
| 42 43 643 | 8/1993 | Germany . |
| 64000042 | 6/1987 | Japan . |

OTHER PUBLICATIONS

Fat. Sci. Technol., 89(3):106–11 (1987).

*Primary Examiner*—Deborah Carr
*Attorney, Agent, or Firm*—Wayne C. Jaeschke; Real J. Grandmaison; Glenn E. J. Murphy

[57] ABSTRACT

A process for the production of end-capped nonionic surfactants corresponding to formula (I):

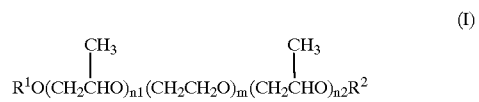

in which $R^1$ is an alkyl or alkenyl group containing 6 to 22 carbon atoms, n1 and n2 independently of one another represent 0 or a number from 1 to 10, m represents a number from 1 to 20 and $R^2$ represents methyl or ethyl, by (a) etherifying a fatty alcohol polyglycol ether corresponding to formula (II):

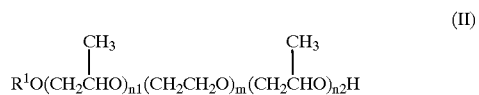

in which $R^1$, n1, n2 and m are as defined above, with a dialkyl sulfate in the presence of a solid substantially water-free base and an alkali metal or alkaline earth metal hydride, (b) adding water to the crude ethers in such a quantity that phase separation occurs, and (c) removing the organic phase.

13 Claims, No Drawings

PROCESS FOR PRODUCING END-GROUP-LOCKED NON-IONIC TENSIDES

This application is a 371 of PCT/EP95/05139 filed Dec. 17, 1995.

BACKGROUND OF THE INVENTION

1. Field of the Invention

This invention relates to a process for the production of end-capped nonionic surfactants by direct etherification of fatty alcohol polyglycol ethers with dialkyl sulfates in the presence of solid bases and hydrides and addition of water for phase separation.

2. Discussion of Related Art

PRIOR ART

In a number of industrial processes, the presence of foam is extremely undesirable. For example, both in the machine washing of beer bottles or milk bottles and in the spray cleaning of automobile panels, not only is the cleaning or degreasing effect of the surface-active formulations used an important factor, the avoidance of foam which can seriously interfere with the operation of machinery is of equal importance—all the more so insofar as highly active, but also high-foaming anionic surfactants are often used.

The problem of controlling foam has been known for some time. Accordingly, various more or less convincing solutions are known from the prior art and may be divided into two groups:

The first group comprises processes involving the addition of defoamers which are often paraffinic hydrocarbons or silicone compounds. So far as the described applications are concerned, however, this is undesirable in most cases. The second group of processes involves the use of surface-active formulations which are themselves low-foaming and which, optionally, may also exhibit defoaming properties. The formulations in question are generally nonionic surfactants or surfactant-like systems such as, for example, fatty alcohol propylene glycol ethers or block polymers of ethylene and propylene glycol which, unfortunately, are not sufficiently biodegradable.

End-capped fatty alcohol polyglycol ethers, so-called "mixed ethers", which are described for example by R. Piorr in Fat. Sci. Technol. 89, 106 (1987), have established themselves on the market as particularly effective low-foaming surfactants. These products are generally butyl-end-capped nonionic surfactants which are known, for example, from EP-A 0 124 815, EP-B 0 303 928, EP-B 0 324 340, EP-A 0 420 802, DE-A 3 928 600 and DE-C 4 243 643.

Methyl mixed ethers occupy a special position. They are methyl-end-capped and are normally prepared by reaction of the corresponding fatty alcohol polyglycol ethers with methyl halides [U.S. Pat. No. 4,587,365, BASF] or dimethyl sulfate.

In this connection, EP 0 302 487 B1 (BASF) describes a one-pot process for the production of end-capped nonionic surfactants in which fatty alcohol polyglycol ethers are reacted with dialkyl sulfates in the presence of aqueous alkali metal hydroxides, the reaction taking place at a temperature of 20 to 60° C. and the concentration of alkali metal hydroxide having to be kept at or above 35% by weight, based on the aqueous phase, throughout the reaction. However, the products contain up to 25% by weight of unreacted starting product and are unacceptable from the point of view of color.

Accordingly, the problem addressed by the present invention was to provide an improved process for the production of end-capped nonionic surfactants of the methyl mixed ether type which would be distinguished by a reduced content of unreacted starting material and by improved color quality.

DESCRIPTION OF THE INVENTION

The present invention relates to a process for the production of end-capped nonionic surfactants corresponding to formula (I):

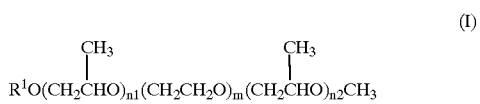

in which $R^1$ is an alkyl and/or alkenyl group containing 6 to 22 carbon atoms, n1 and n2 independently of one another stand for 0 or numbers of 1 to 10 and m stands for numbers of 1 to 20, by reaction of alcohol alkoxylates with dialkyl sulfates, in which (a) fatty alcohol polyglycol ethers corresponding to formula (II):

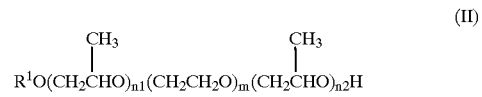

in which $R^1$, n1, n2 and m are as defined above, are etherified with dialkyl sulfates (IV) in the presence of solid substantially water-free bases (III) and alkali metal and/or alkaline earth metal hydrides, (b) water is added to the crude ethers in such a quantity that phase separation occurs and (c) the organic useful phases are removed by methods known per se.

A process in which alcoholate formation and etherification are carried out in the presence of aqueous bases is already known from the prior art. Surprisingly, it has been found to be of far greater advantage to carry out the "one-pot reaction", i.e. formation of the alcoholate and its further reaction with the dialkyl sulfate, in the presence of solid substantially water-free bases and hydrides because products having a relatively low content of unreacted starting material can be obtained. These products are additionally distinguished by improved color quality.

Fatty alcohol Polyglycol ethers

Fatty alcohol polyglycol ethers are known nonionic surfactants which may be obtained by the relevant methods of preparative organic chemistry, for example by addition of alkylene oxides to fatty alcohols. The ethers may have a conventional broad homolog distribution or a narrow homolog distribution, depending on the alkoxylation catalyst.

Typical examples of fatty alcohol polyglycol ethers which may be used as starting materials for the purposes of the invention are products of the addition of 5 to 15 moles of ethylene oxide and optionally 1 mole of propylene oxide to caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol and erucyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols.

Particularly preferred starting materials are fatty alcohol polyglycol ethers corresponding to formula (II) in which $R^1$ is an alkyl group containing 12 to 18 carbon atoms, n1 stands for 0, m stands for numbers of 5 to 15 and n2 stands for 1 or in which $R^1$ is an alkyl group containing 6 to 10 carbon atoms, n1 stands for 1, m stands for numbers of 5 to 15 and n2 stands for 0.

Bases

Suitable bases are, above all, the oxides, hydroxides and carbonates of the alkali and/or alkaline earth metals. Typical examples are lithium hydroxide, sodium carbonate, sodium hydrogen carbonate, magnesium oxide, magnesium hydroxide, calcium oxide and calcium hydroxide. Sodium hydroxide and/or potassium hydroxide are preferred bases, potassium hydroxide being particularly preferred. The bases are used as solid products, i.e. for example as beads, flakes or pellets, and from their production generally have a water content of less than 15% by weight and, more particularly, less than 10% by weight. A water content of this order is tolerable in the process according to the invention although, basically, water-free products would be preferable but, unfortunately, are not readily available on an industrial scale.

It has proved to be of advantage to use the fatty alcohol polyglycol ethers (II) and the bases (III) in a molar ratio of 1:1.0 to 1:1.5 and preferably in a molar ratio of 1:1.1 to 1:1.4.

Alkali metal and/or alkaline earth metal hydrides

According to the present invention, the etherification is carried out in the presence of alkali metal and/or alkaline earth metal hydrides, preferably borohydrides, which leads to substantially colorless products. Typical examples of suitable borohydrides are potassium borohydride and magnesium borohydride, sodium borohydride being particularly suitable. Other suitable stabilizers are lithium alanate and hypophosphorous acid and alkali metal salts thereof—particularly in combination with sodium borohydride. The hydrides are normally used in quantities of 100 to 1000 ppm and, more particularly, in quantities of 300 to 700 ppm, based on the fatty alcohol polyglycol ethers.

Dialkyl sulfates

Dialkyl sulfates in the context of the present invention are diethyl sulfate and, in particular, dimethyl sulfate. Mixtures of dimethyl and diethyl sulfate and higher alkyl sulfates—where they are available in commercial quantities—are also suitable in principle as alkylating agents for the process according to the invention. The fatty alcohol polyglycol ethers (II) and the dialkyl sulfates (IV) are preferably used in a molar ratio of 1:1.0 to 1:1.5 and, more preferably, in a molar ratio of 1:1.1 to 1:1.4.

Etherification

The etherification is carried out as a "one-pot reaction", i.e. formation of the alcoholate from the fatty alcohol polyglycol ether and the base and its further reaction with the dialkyl sulfate take place in parallel. The etherification is preferably carried out at a temperature of 20 to 100° C. and more preferably at a temperature of 40 to 50° C.

Phase separation and aftertreatment

The aftertreatment of the crude alkylation products with water has two objectives. Firstly, the quantity of inorganic salt formed during the etherification step migrates into the aqueous phase; secondly, unreacted dialkyl sulfate is decomposed. To this end, it has proved to be of advantage to carry out the phase separation at a temperature of 40 to 98° C. and, more particularly, 70 to 85°C. After the phase separation, the ether is normally dried and unreacted base is filtered off. If necessary, the content of free alkylating agent can be further reduced by adding 0.1 to 1% by weight of an amino compound, for example ammonia, glycine or an alkanolamine, to the ether—optionally even before phase separation.

Commercial Applications

The end-capped nonionic surfactants obtainable by the process according to the invention are distinguished by excellent wetting power, are extremely low-foaming and are capable of defoaming above all formulations containing anionic surfactants. Accordingly, they are particularly suitable for the production of machine bottle washing formulations in which they may be present in quantities of 1 to 50% by weight and preferably 5 to 35% by weight, based on the formulation.

The following Examples are intended to illustrate the invention without limiting it in any way.

EXAMPLES

Examples 1 to 4

In a three-necked flask equipped with a dropping funnel, stirrer and reflux condenser, dimethyl sulfate was added to a mixture of 500 g of $C_{12/14}$ cocoalcohol+6EO, 500 ppm of sodium borohydride (based on the polyglycol ether) and alkali metal hydroxide flakes, followed by stirring first for 1 hour at 45°C., then for 2 hours at 50° C. and finally for 1 hour at 60° C. 500 g of water were then added, the mixture was heated to 80–85° C. and was then stirred for another 2 hours, during which phase separation occurred, the sulfate salt formed being almost completely dissolved in the aqueous phase. After phase separation, the organic useful phase was dried in vacuo and then filtered. Particulars of the quantity ratios and characteristic data of the products can be found in Table 1. The percentages represent % by weight.

Example 5

Example 1 was repeated using octanol+1PO+10EO. The results are set out in Table 1.

Example 6

Example 1 was repeated using $C_{12/14}$ cocofatty alcohol+10EO+1PO. The results are set out in Table 1.

Comparison Example C1

Example 1 was repeated without the addition of sodium borohydride. The results are set out in Table 1.

Comparison Example C2

Example 1 was repeated without the addition of sodium borohydride and with a corresponding quantity of 50% by weight potassium hydroxide solution instead of the KOH flakes. The results are set out in Table 1.

TABLE 1

Etherification with Dimethyl Sulfate

| Ex. | Base | F:Base | F:DMS | Yield % of Theoretical | Salt % | Color Gard. |
|---|---|---|---|---|---|---|
| 1 | KOH | 1:1.27 | 1:1.15 | 92 | <1 | <1 |
| 2 | KOH | 1:1.30 | 1:1.20 | 91 | <1 | <1 |
| 3 | KOH | 1:1.40 | 1:1.30 | 90 | <1 | <1 |
| 4 | NaOH | 1:1.30 | 1:1.20 | 90 | <1 | <1 |
| 5 | KOH | 1:1.27 | 1:1.15 | 91 | <1 | <1 |
| 6 | KOH | 1:1.27 | 1:1.15 | 89 | <1 | <1 |
| C1 | KOH | 1:1.27 | 1:1.15 | 92 | <1 | 11 |
| C2 | KOH | 1:1.27 | 1:1.15 | 76 | <1 | Red |

Legend:
F: Base = Molar ratio of fatty alcohol polyglycol ether to base
F: DMS = Molar ratio of fatty alcohol polyglycol ether to dimethyl sulfate
Salt = Content of inorganic sulfate in the product
Color = Gardner color number

What is claimed is:

1. An nonionic surfactant compound corresponding to formula (I):

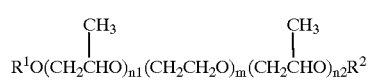

(I)

in which $R^1$ is an alkyl or alkenyl group containing 6 to 22 carbon atoms, n1 and n2 independently of one another represent 0 or a number from 1 to 10, m represents a number from 1 to 20, and $R^2$ represents methyl or ethyl.

2. A compound as in claim 1 wherein $R^1$ is an alkyl group containing 12 to 18 carbon atoms, n1 represents 0, m represents a number from 5 to 15, and n2 represents 1.

3. A compound as in claim 1 wherein $R^1$ is an alkyl group containing 6 to 10 carbon atoms, n1 represents 1, m represents a number from 5 to 15 and, n2 represents 0.

4. A process for the production of end-capped nonionic surfactants corresponding to formula (I):

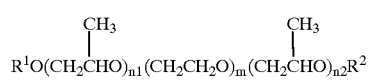

(I)

in which $R^1$ is an alkyl or alkenyl group containing 6 to 22 carbon atoms, n1 and n2 independently of one another represent 0 or a number from 1 to 10, m represents a number from 1 to 20 and $R^2$ represents methyl or ethyl, comprising (a) etherifying a fatty alcohol polyglycol ether corresponding to formula (II):

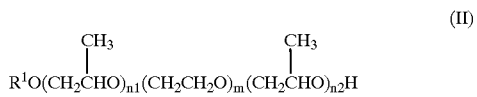

(II)

in which $R^1$, n1, n2 and m are as defined above, with a dialkyl sulfate in the presence of a solid substantially water-free base and an alkali metal or alkaline earth metal hydride, (b) adding water to the crude ethers in such a quantity that phase separation occurs, and (c) removing the organic phase.

5. A process as in claim 4 wherein in said fatty alcohol polyglycol ether corresponding to formula (II), $R^1$ is an alkyl group containing 12 to 18 carbon atoms, n1 represents 0, m represents a number from 5 to 15 and n2 represents 1.

6. A process as in claim 4 wherein in said fatty alcohol polyglycol ether corresponding to formula (II), $R^1$ is an alkyl group containing 6 to 10 carbon atoms, n1 represents 1, m represents a number from 5 to 15 and n2 represents 0.

7. A process as in claim 4 wherein said base is sodium hydroxide or potassium hydroxide.

8. A process as in claim 4 wherein said fatty alcohol polyglycol ether corresponding to formula (II) and said base are present in a molar ratio of 1:1.0 to 1:1.5.

9. A process as in claim 4 wherein said dialkylsulfate is dimethyl sulfate or diethyl sulfate.

10. A process as in claim 4 wherein said fatty alcohol polyglycol ether corresponding to formula (II) and said dialkyl sulfate are present in a molar ratio of 1:1.0 to 1:1.5.

11. A process as in claim 4 wherein said etherifying step is conducted at a temperature of 20° C. to 100° C.

12. A process as in claim 4 wherein the phase separation is conducted at a temperature of 70° C. to 98°C.

13. A process as in claim 4 wherein 0.1 to 1% by weight of an amino compound is added to said organic phase to destroy unreacted dialkyl sulfate.

* * * * *